US011850036B2

(12) United States Patent
Takatori

(10) Patent No.: US 11,850,036 B2
(45) Date of Patent: Dec. 26, 2023

(54) AIRWAY ADAPTOR AND RESPIRATORY FLOW RATE SENSOR

(71) Applicant: Nihon Kohden Corporation, Tokyo (JP)

(72) Inventor: Fumihiko Takatori, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 0 days.

(21) Appl. No.: 15/266,463

(22) Filed: Sep. 15, 2016

(65) Prior Publication Data

US 2017/0086708 A1    Mar. 30, 2017

(30) Foreign Application Priority Data

Sep. 24, 2015  (JP) ................ 2015-186785

(51) Int. Cl.
| | | |
|---|---|---|
| A61B 5/087 | (2006.01) | |
| G01F 1/684 | (2006.01) | |
| G01F 1/40 | (2006.01) | |
| A61M 16/08 | (2006.01) | |
| A61M 16/00 | (2006.01) | |

(Continued)

(52) U.S. Cl.
CPC ............ *A61B 5/0873* (2013.01); *A61B 5/082* (2013.01); *A61B 5/087* (2013.01); *A61B 5/091* (2013.01); *A61B 5/097* (2013.01); *A61M 16/0003* (2014.02); *A61M 16/0078* (2013.01); *A61M 16/04* (2013.01); *A61M 16/06* (2013.01);

(Continued)

(58) Field of Classification Search
CPC .... A61B 5/097; A61B 5/087; A61M 16/0816; A61M 2205/3306
See application file for complete search history.

(56) References Cited

U.S. PATENT DOCUMENTS

| | | |
|---|---|---|
| 5,347,843 A | 9/1994 | Orr et al. |
| 5,379,650 A | 1/1995 | Kofoed et al. |

(Continued)

FOREIGN PATENT DOCUMENTS

| | | |
|---|---|---|
| JP | H09-502025 A | 2/1997 |
| JP | 2009-028551 A | 2/2009 |

(Continued)

OTHER PUBLICATIONS

Extended European Search Report issued in Patent Application No. EP 16 18 8936 dated Feb. 14, 2017.

(Continued)

*Primary Examiner* — Tse W Chen
*Assistant Examiner* — Michael A Catina
(74) *Attorney, Agent, or Firm* — Pearne & Gordon LLP

(57) ABSTRACT

An airway adaptor includes a tubular member to which a measuring section configured to measure a flow rate of a respiratory gas of a subject is to be attached. The tubular member includes: a gas passage through which the respiratory gas to pass; and a resistance portion which is configured to generate a differential pressure in the respiratory gas passing through the gas passage, the resistance portion includes at least two partition members which are disposed in the gas passage along an axial direction of the tubular member and which are separated from one another, and side surfaces of the partition members are separated from an inner wall surface of the gas passage.

10 Claims, 14 Drawing Sheets

(51) Int. Cl.
*A61B 5/08* (2006.01)
*A61B 5/091* (2006.01)
*A61B 5/097* (2006.01)
*A61M 16/04* (2006.01)
*A61M 16/06* (2006.01)

(52) U.S. Cl.
CPC ............ *A61M 16/085* (2014.02); *G01F 1/40* (2013.01); *G01F 1/6842* (2013.01); *A61M 2205/3334* (2013.01)

(56) References Cited

U.S. PATENT DOCUMENTS

| | | | |
|---|---|---|---|
| 5,535,633 A | 7/1996 | Kofoed et al. | |
| 5,789,660 A | 8/1998 | Kofoed et al. | |
| 5,979,247 A * | 11/1999 | Kizawa | G01F 1/42 |
| | | | 73/861.53 |
| 6,312,389 B1 | 11/2001 | Kofoed et al. | |
| 6,325,978 B1 | 12/2001 | Labuda et al. | |
| 6,512,581 B1 * | 1/2003 | Yamamori | A61B 5/097 |
| | | | 356/246 |
| 6,601,460 B1 | 8/2003 | Materna | |
| 6,815,211 B1 | 11/2004 | Blazewicz et al. | |
| 2001/0031224 A1 | 10/2001 | Labuda et al. | |
| 2002/0029003 A1 | 3/2002 | Mace et al. | |
| 2004/0013570 A1 | 1/2004 | Labuda et al. | |
| 2007/0225612 A1 | 9/2007 | Mace et al. | |
| 2010/0036272 A1 | 2/2010 | Mace et al. | |
| 2011/0028858 A1 * | 2/2011 | Dainobu | A61B 5/097 |
| | | | 600/532 |
| 2011/0094513 A1 | 4/2011 | Takatori | |
| 2012/0192642 A1 | 8/2012 | Speldrich et al. | |
| 2012/0325214 A1 * | 12/2012 | Weckstrom | A61B 5/0833 |
| | | | 128/205.23 |
| 2016/0331272 A1 * | 11/2016 | Ahmad | A61B 5/082 |

FOREIGN PATENT DOCUMENTS

| | | |
|---|---|---|
| JP | 2010-187816 A | 9/2010 |
| JP | 2011-115543 A | 6/2011 |

OTHER PUBLICATIONS

Japanese Office action issued in Japanese Patent Application No. 2015-186785 dated May 7, 2019.

* cited by examiner

AIRWAY ADAPTOR AND RESPIRATORY FLOW RATE SENSOR

CROSS-REFERENCE TO RELATED APPLICATION(S)

This application is based upon and claims the benefit of priority from prior Japanese patent application No. 2015-186785, filed on Sep. 24, 2015, the entire contents of which are incorporated herein by reference.

BACKGROUND

The presently disclosed subject matter relates to a respiratory flow rate sensor which measures the flow rate of the respiratory gas of the subject, and an airway adaptor which is to be used in the respiratory flow rate sensor.

A ventilation method has been performed in which, with respect to a subject in a hypoventilated state or a respiratory arrest state, a mask with an air supply bag (an Ambu bag, a Jackson Rees bag, or the like) covers an area extending from the mouth cavity of the subject to the nasal cavity, and a medical person or the like presses the air supply bag to supply the air to the lungs of the subject (see JP-A-2011-115543).

In the case where the related-art ventilation method is performed, when a gap exists between the mask and the face of the subject, ventilation is not adequately performed. In ventilation, therefore, a medical person or the like visually checks whether the chest of the subject expands or not, and whether the thorax is raised or not.

When ventilation failure or the like occurs, an artificial respirator has been used.

The visual check is effective in an adult in whom the ventilation volume is large. In the case of an infant or baby in whom the ventilation volume is small, however, it is sometimes difficult to perform the visual check. Therefore, the inventor of the present application tried to measure the flow rate in a subject under ventilation by using a related-art differential pressure flowmeter. However, there was the following problem.

In order to obtain a differential pressure signal which is necessary for accurately measuring a small ventilation volume of an infant or a baby, the orifice (an opening of an orifice plate) of the flowmeter must be narrowed. When the orifice is narrowed, however, the resistance of the gas passage in the flowmeter is increased, and, because of the increased resistance, it is difficult for the infant, the baby, or the like to discharge the expiration.

SUMMARY

The presently disclosed subject matter may provide an airway adaptor and respiratory flow rate sensor which, while preventing the resistance of a gas passage from being increased, can obtain a differential pressure signal that is necessary for measuring a relatively small ventilation volume.

The airway adaptor may include a tubular member to which a measuring section configured to measure a flow rate of a respiratory gas of a subject is to be attached. The tubular member includes: a gas passage through which the respiratory gas to pass; and a resistance portion which is configured to generate a differential pressure in the respiratory gas passing through the gas passage. The resistance portion includes at least two partition members which are disposed in the gas passage along an axial direction of the tubular member and which are separated from one another. Side surfaces of the partition members are separated from an inner wall surface of the gas passage.

DETAILED DESCRIPTION OF EXEMPLARY EMBODIMENTS

Figure 1:
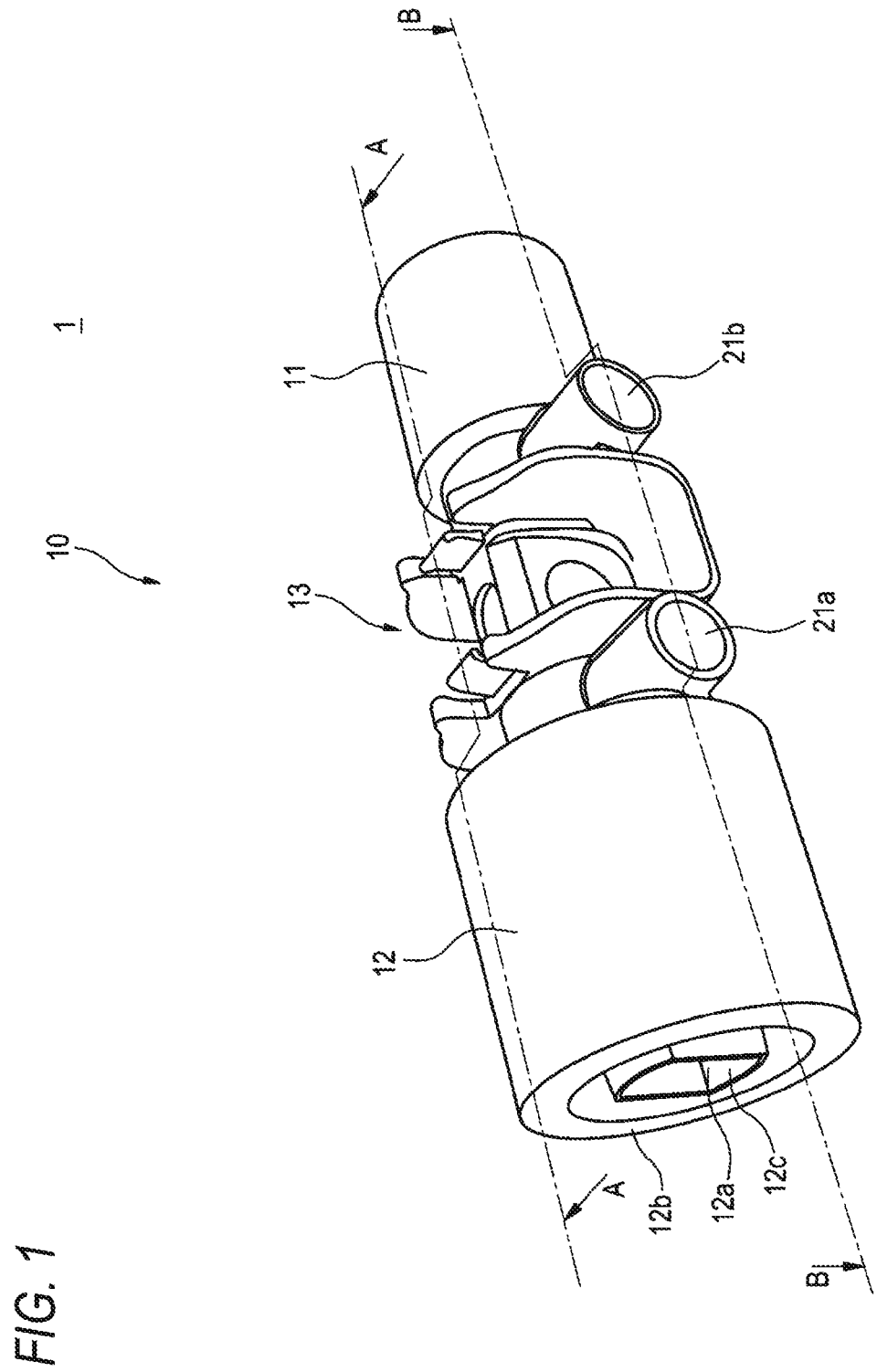
FIG. 1 is a view illustrating an airway adaptor of an embodiment of the presently disclosed subject matter.
Figure 2:
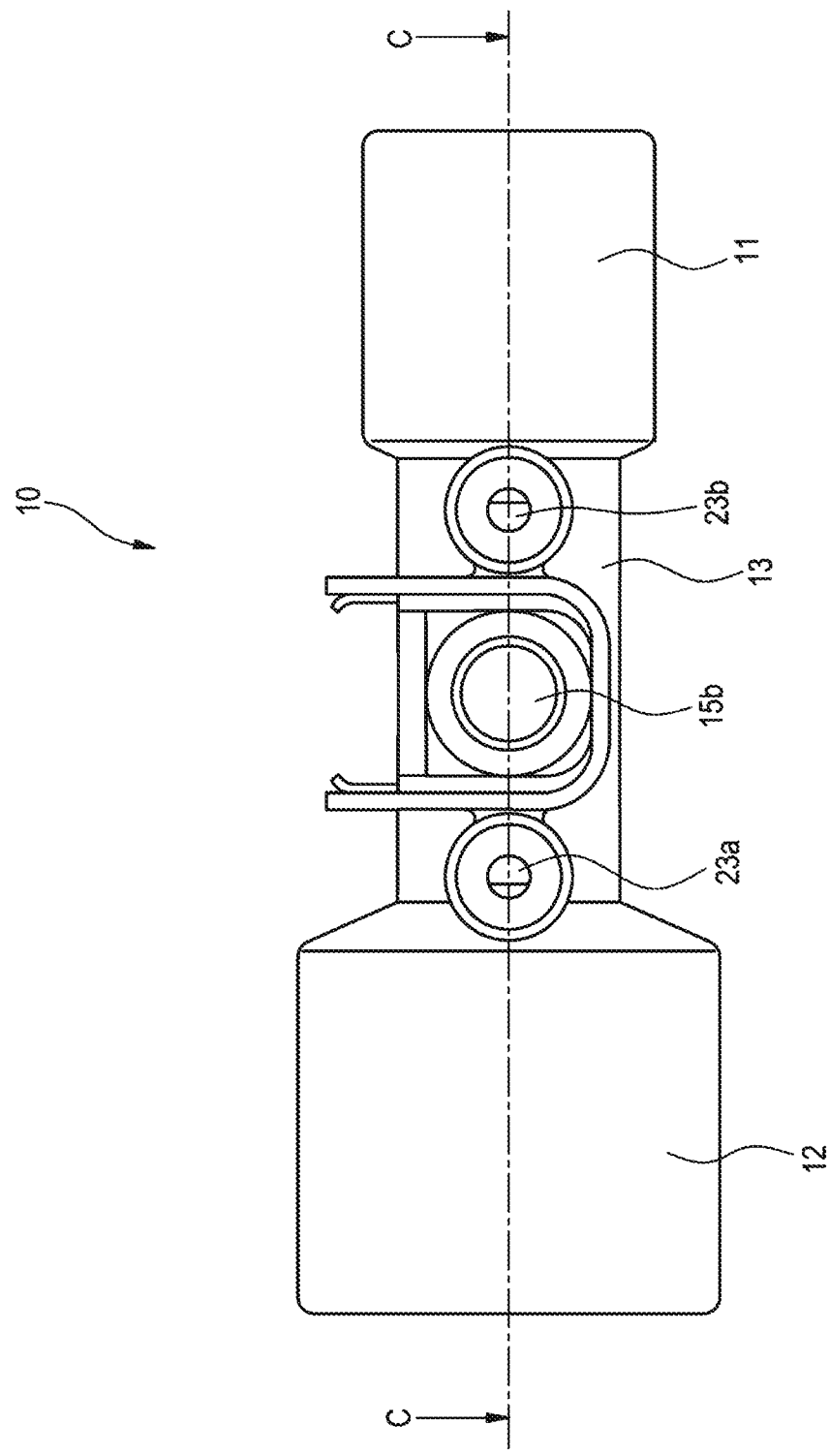
FIG. 2 is a top view of the airway adaptor.
Figure 3:
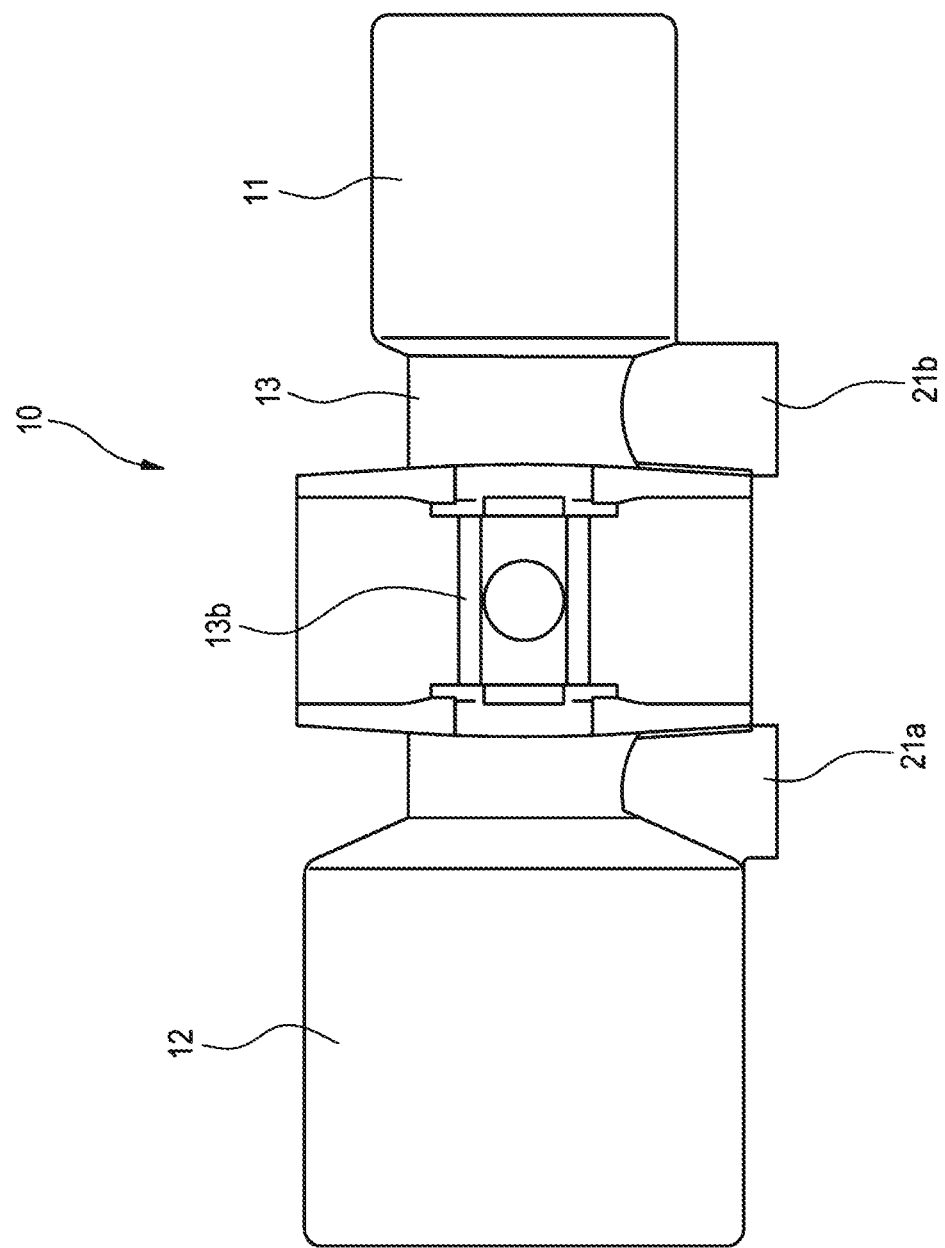
FIG. 3 is a front view of the airway adaptor.
Figure 4:
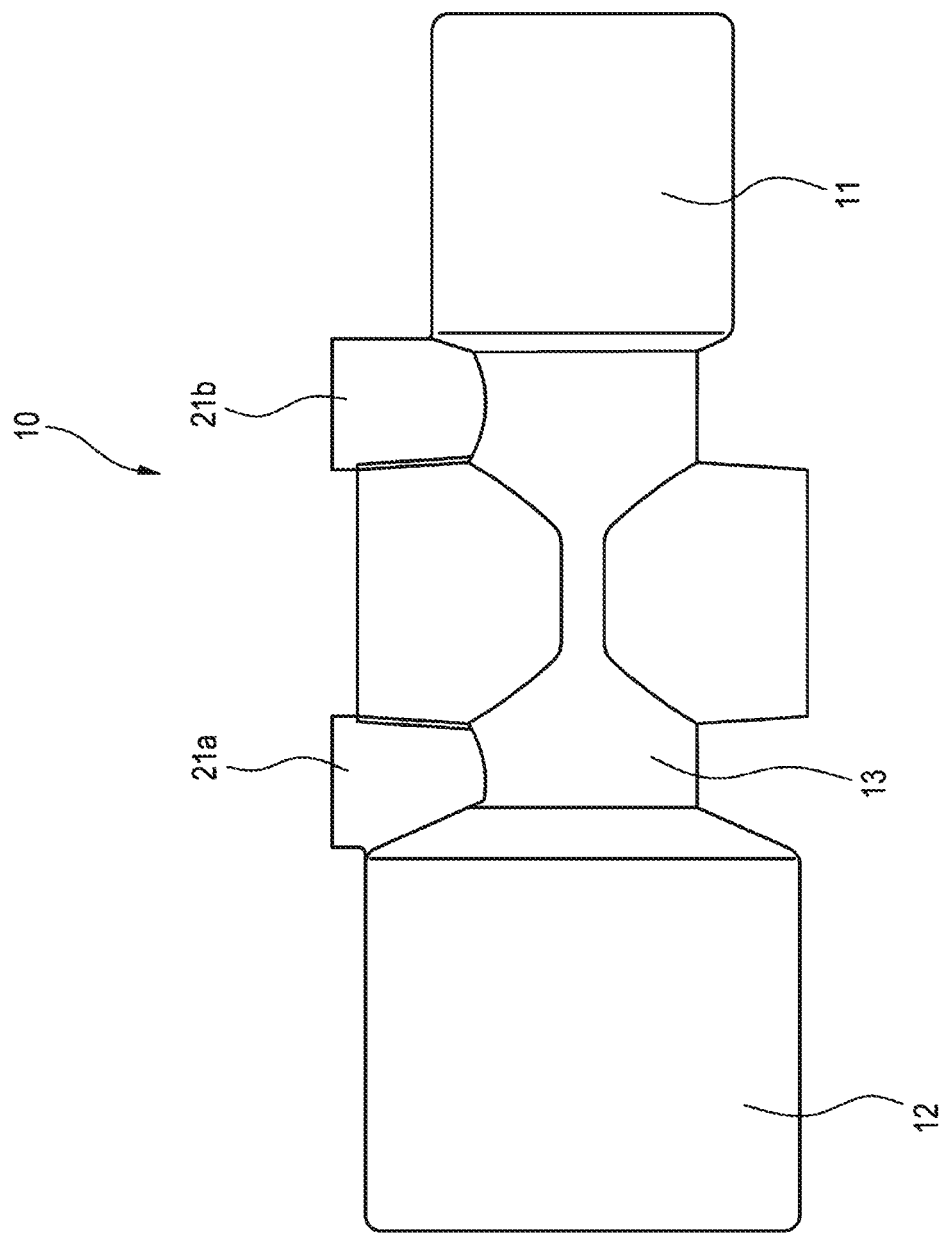
FIG. 4 is a bottom view of the airway adaptor.
Figure 5:
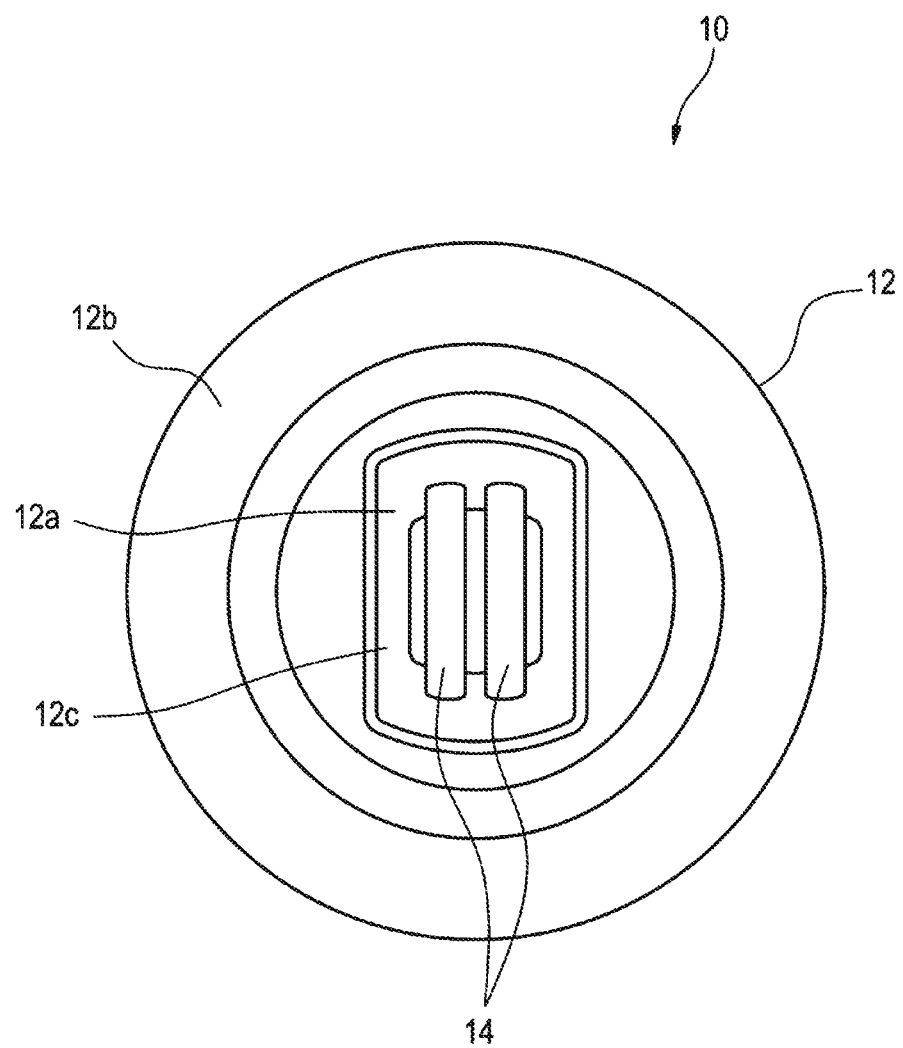
FIG. 5 is a left side view of the airway adaptor.
Figure 6:
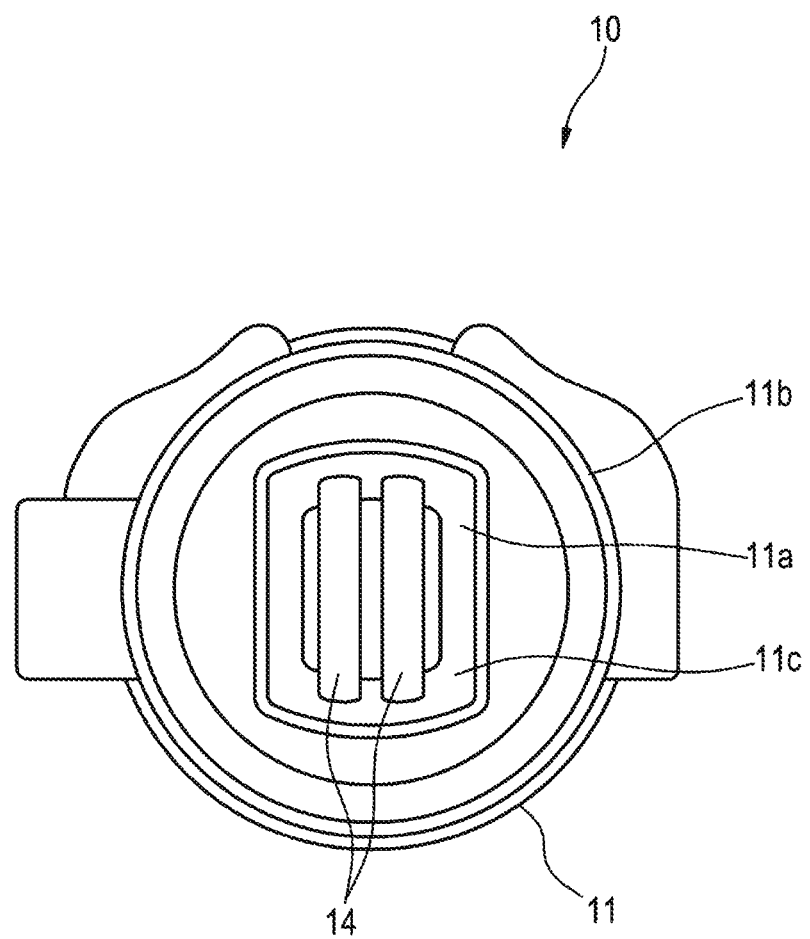
FIG. 6 is a right side view of the airway adaptor.

Hereinafter, an embodiment will be described in detail with reference to the drawings. An airway adaptor 1 is used in, for example, measuring the flow rate of the respiratory gas of a subject who requires respiratory management. Particularly, the airway adaptor 1 may be used for a subject in whom the ventilation volume is small (for example, an infant, a baby, or an aged person).

As illustrated in FIGS. 1 to 8, the airway adaptor 1 may include a tubular member 10 which generally has an approximately tubular shape. A measuring section for measuring the flow rate of the respiratory gas is to be connected to the tubular member 10.

The tubular member 10 is configured by a first adaptor section 11, a second adaptor section 12, and an attaching section 13.

The first adaptor section 11 is disposed in one end side of the tubular member 10, and has a cylindrical shape (see FIGS. 1, and 6 to 8). In the first adaptor section 11, a first adaptor gas passage 11a through which the respiratory gas is to flow is disposed along the axial direction of the tubular member 10. In the embodiment, the first adaptor gas passage 11a is formed into a rectangular shape. A first adaptor connecting portion 11b which is formed so as to cover the first adaptor gas passage 11a is disposed outside the first adaptor gas passage 11a.

The first adaptor section 11 is connected to an external apparatus (an example of the inspiration supplying section) such as an Ambu bag, a Jackson Rees bag, or an artificial respirator through the first adaptor connecting portion 11b. The air (inspiration into the subject) supplied from the external apparatus is introduced into the first adaptor gas passage 11a through an opening 11c of the first adaptor gas passage 11a.

The second adaptor section 12 is disposed in the other end side of the tubular member 10 which is opposite to the first adaptor section 11, and has a cylindrical shape (see FIGS. 1, 5, 7, and 8). The second adaptor section 12 is formed into a cylindrical shape having a diameter which is larger than that of the first adaptor section 11. In the second adaptor section 12, a second adaptor gas passage 12*a* through which the respiratory gas is to flow is disposed along the axial direction of the tubular member 10. In the embodiment, the second adaptor gas passage 12*a* is formed into a rectangular shape. A second adaptor connecting portion 12*b* which is formed so as to cover the second adaptor gas passage 12*a* is disposed outside the second adaptor gas passage 12*a*.

The second adaptor section 12 is connected to an apparatus (an example of the expiration outputting section) on the side of the subject such as a tracheal tube or a mask through the second adaptor connecting portion 12*b*. The air (expiration) discharged from the subject is introduced into the second adaptor gas passage 12*a* through an opening 12*c* of the second adaptor gas passage 12*a*.

The attaching section 13 is disposed in a middle portion of the tubular member 10, and located between the first adaptor section 11 and the second adaptor section 12. In the attaching section 13, an attaching-section gas passage 13*a* through which the respiratory gas is to flow is disposed along the axial direction of the tubular member 10 (see FIG. 8).

A plurality (in the embodiment, two) of plate-like members 14 (an example of the partition members) are disposed in the attaching-section gas passage 13*a* (see FIGS. 5 to 8). The plate-like members 14 are juxtaposed to each other along the axial direction of the tubular member 10 in a state where they are separated from each other. In the embodiment, the two plate-like members 14 are disposed parallel to each other. The plate-like members 14 are disposed so that the side surfaces 14*a* of the plate-like members 14 are directed toward the front (or the back) of the tubular member 10. In the embodiment, projections 15 are formed on the inner wall of the attaching-section gas passage 13*a* to narrow (or constrict) the attaching-section gas passage 13*a*, and the two plate-like members 14 are disposed between the both projections 15.

The side surfaces 14*a* of the plate-like members 14 are disposed in a state where the side surfaces are separated from the the inner wall surface (the surfaces 15*a* of the projections 15) of the attaching-section gas passage 13*a*. The side surfaces 14*a* are disposed parallel to the axial direction of the tubular member 10. Since the plate-like members 14 are disposed, the interior of the attaching-section gas passage 13*a* has a configuration where the interior is partitioned into a plurality (in the embodiment, three) of gas passages which are juxtaposed to one another so as to extend along the axial direction of the tubular member 10. The six surfaces which are the sum of the both side surfaces of the two plate-like members 14 and the surfaces 15*a* of the two projections 15 are disposed along the axial direction of the tubular member 10 (along the flow direction of the respiratory gas)

The members which are disposed in the attaching-section gas passage 13*a* are not limited to the above-described plate-like members 14, as far as they have surfaces which extend along the axial direction of the tubular member 10. For example, a plurality of tubular members each having a curved surface may be disposed.

Figure 7:
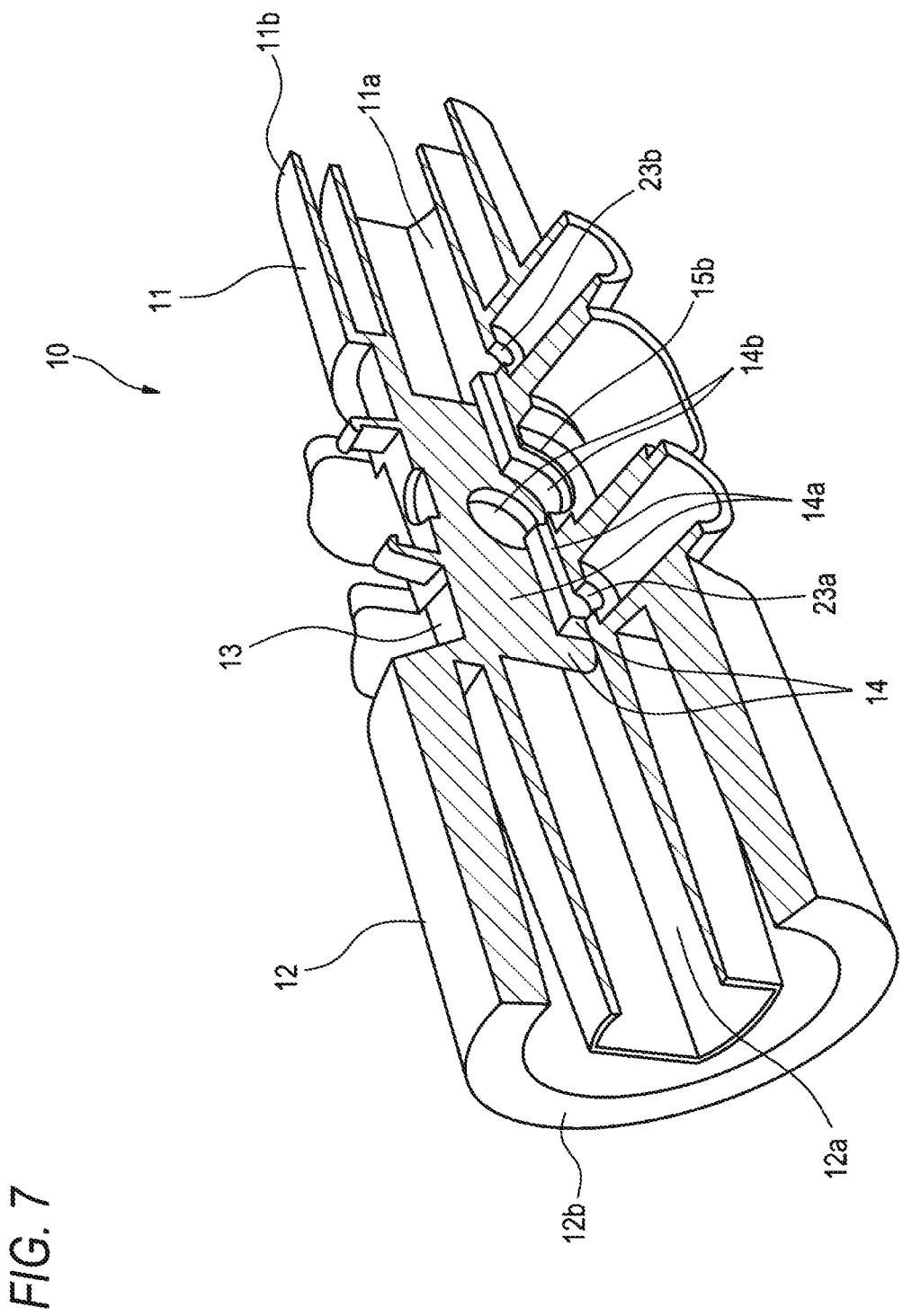
FIG. 7 is a fragmentary sectional view taken along lines A-A and B-B in FIG. 1.
Figure 8:
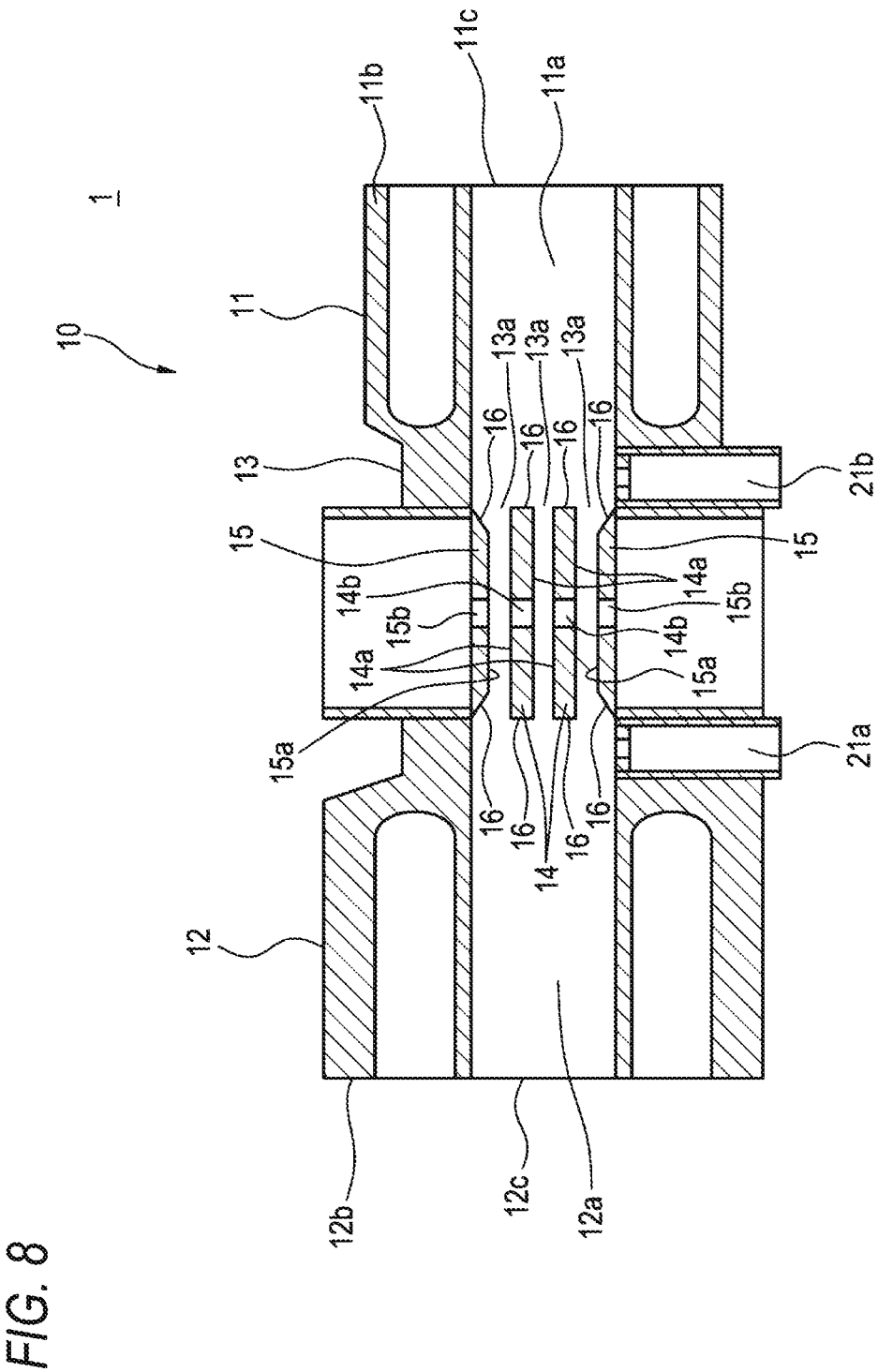
FIG. 8 is a sectional view taken along line C-C in FIG. 2.

Holes 14*b* are formed in substantially middle portions of the two plate-like members 14, respectively (see FIGS. 7 and 8). The holes 14*b* are disposed so as to be opposed to each other, and a detection light beam which is emitted from the outside of the tubular member 10 can pass through the holes. Windows 15*b* which are openings communicating with the attaching-section gas passage 13*a* are formed so as to be opposed to each other in the wall of the attaching section 13 (the walls of the portions where the projections 15 are formed) (see FIGS. 2, 7, and 8). The holes 14*b* and the windows 15*b* are formed so as to have a substantially same size, and arranged on the same axis. measuring section which emits and receives the detection light beam to measure the concentration of a specific component of the respiratory gas can be attached to the portion 13*b* (see FIG. 3) where the windows 15*b* of the attaching section 13 are formed.

Pressure take-out ports 21*a*, 21*b* which extend in a direction perpendicular to the axial direction of the tubular member 10 are disposed in the both end sides of the attaching section 13 in the axial direction of the tubular member 10, respectively (see FIGS. 1, 3, 4, and 8). The pressure take-out ports 21*a*, 21*b* are passed through the wall of the attaching-section gas passage 13*a*. The measuring section for measuring the flow rate of the respiratory gas can be attached to the airway adaptor through the pressure take-out ports 21*a*, 21*b*.

The first adaptor gas passage 11*a* of the first adaptor section 11 is coupled to one end of the attaching-section gas passage 13*a* of the attaching section 13 (see FIGS. 7 and 8). The second adaptor gas passage 12*a* of the second adaptor section 12 is coupled to the other end of the attaching-section gas passage 13*a* which is opposite to the first adaptor gas passage 11*a*. In the tubular member 10, the first adaptor gas passage 11*a*, the attaching-section gas passage 13*a*, and the second adaptor gas passage 12*a* form the gas passage which communicatively extends in the axial direction of the tubular member 10.

In the gas passage of the thus configured tubular member 10, the inspiration which is supplied from the external apparatus toward the subject passes through the first adaptor gas passage 11*a* and the attaching-section gas passage 13*a*, and then reaches the second adaptor gas passage 12*a*. The expiration discharged from the subject passes through the second adaptor gas passage 12*a* and the attaching-section gas passage 13*a* to reach the first adaptor gas passage 11*a*.

In the case where respiratory ventilation of the patient is performed, the flow rate is measured based on the differential pressure by using a respiratory flow rate sensor. There is available an orifice flow meter in which an orifice plate having an opening is used, and the flow rate is calculated based on the difference between the pressures of the respiratory gas in front and rear of the orifice plate. In the respiratory gas, the relationship of the flow rate and the differential pressure is indicated by following Expression 1.

$$Q = k\sqrt{\Delta P} \quad \text{(Expression 1)}$$

where Q indicates the flow rate, P indicates the differential pressure, and k indicates a constant.

Among subjects who are to be subjected to respiratory ventilation, there are not only adults in whom the ventilation volume is relatively large, but also subjects in whom the ventilation volume is small, such as infants, babies, and aged persons. In the case where respiratory ventilation is performed on an infant, baby, or the like in whom the ventilation volume is small, it is particularly important to accurately adjust the ventilation volume. In order to obtain a differential pressure signal which is necessary for accurately measuring the ventilation volume, the opening of the orifice plate must be narrowed. When the opening is narrowed, however, the resistance of the gas passage in the flowmeter is increased, and, because of the increased resistance, it is difficult for the infant, the baby, or the like to discharge the expiration.

Therefore, the inventor has studied a configuration where a differential pressure signal which is necessary for accurately measuring the ventilation volume can be obtained, and an infant, baby, or the like can discharge the expiration without difficulty. In a configuration for obtaining a necessary a differential pressure signal, then, attention has focused on factors other than the aperture (size) of the opening.

Figure 9A:
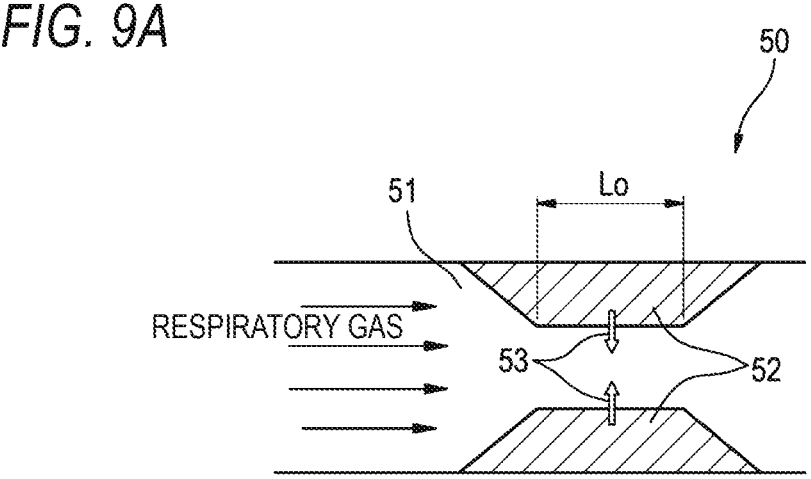
FIGS. 9A and 9B are views illustrating the function of a related-art configuration.
Figure 9B:
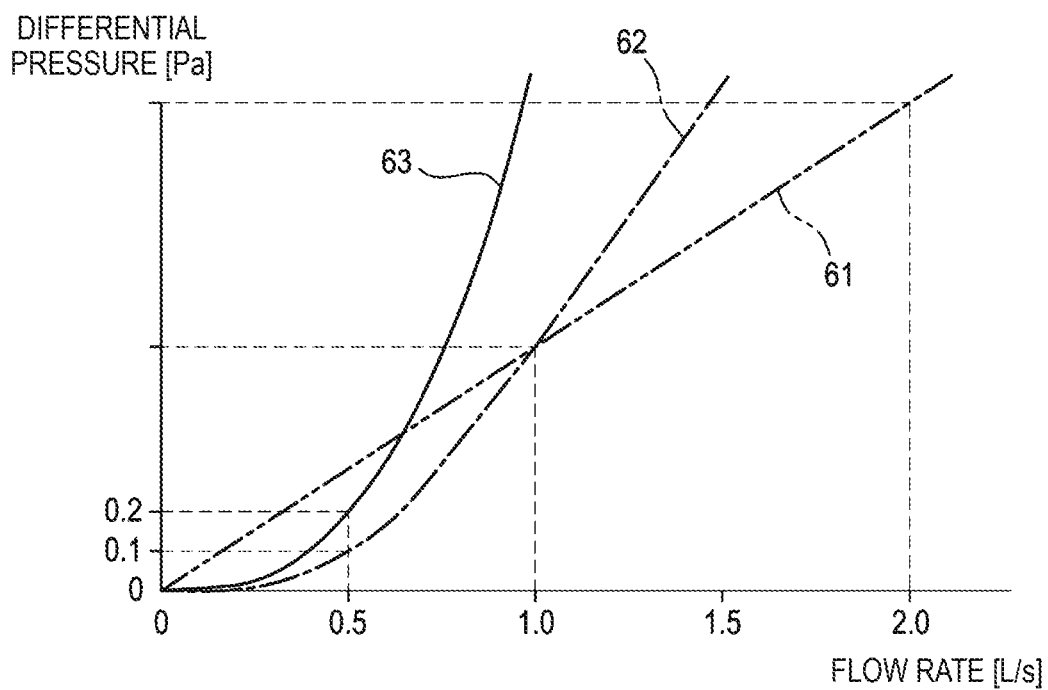

FIG. 9A illustrates an example of a tubular member 50 in which projections 52 are opposedly disposed on the inner wall of a gas passage 51. Each of the projections 52 has a length Lo extending along the flow direction of the respiratory gas. FIG. 9B illustrates a graph of the relationship between the flow rate and the differential pressure in the case where the respiratory gas flows through the gas passage 51 having the configuration of FIG. 9A. In this case, the relationship between the flow rate (y) and the differential pressure (x) can be modeled by, for example, a quadratic function expression of $y=ax^2+bx$.

In the case where the flow rate is measured based on the differential pressure, in order to ensure the measurement accuracy, it is preferable that the relationship between the flow rate and the differential pressure is the relationship of a linear function line 61 in the graph of FIG. 9B. In existing respiratory flow rate sensors which measure the flow rate of the respiratory gas, it is often that the measurement is performed in a range where the ventilation volume is relatively large (for example, a flow rate of 1.0 [L/S] or more). In the range, the value is changed in a manner similar to the linear function line 61 as indicated by a quadratic function curve 62 in the graph of FIG. 9B. Ina range where the ventilation volume is relatively small (for example, a flow rate of 1.0 [L/S] or less), however, the value is changed remotely from the linear function line 61 as indicated by the quadratic function curve 62 (the differential pressure is less changed as compared with a change of the flow rate). In the range where the value is changed in this manner, in the case where noises are caused in the differential pressure output by external factors or the like, the value of the flow rate which is calculated based on the differential pressure is likely to be unstable.

In such a case, also in the configuration of FIG. 9A, when the heights of the projections 52 are changed in the directions of the arrows 53 (the aperture of the gas passage 51 is changed), it is possible to cause the value of the differential pressure in the range where the flow rate is 1.0 [L/S] or less, to become close to the linear function line 61 as indicated by a quadratic function curve 63. When only the size (aperture) of the gas passage 51 is changed, however, the resistance to the respiratory gas flowing through the gas passage 51 is largely increased. Moreover, the differential pressure is largely changed in a range where a large flow rate is large, and therefore the measurement in the range of a large flow rate is hardly performed.

In the analysis in which actual measurements are performed, and the quadratic function curve ($y=ax^2+bx$) is approximated by a linear function line, the inventor has focused attention on the fact that the shifting of the quadratic function curve is affected by the surface areas of the projections 52 having the length to in addition to the aperture (size) of the gas passage 51.

Figure 10A:
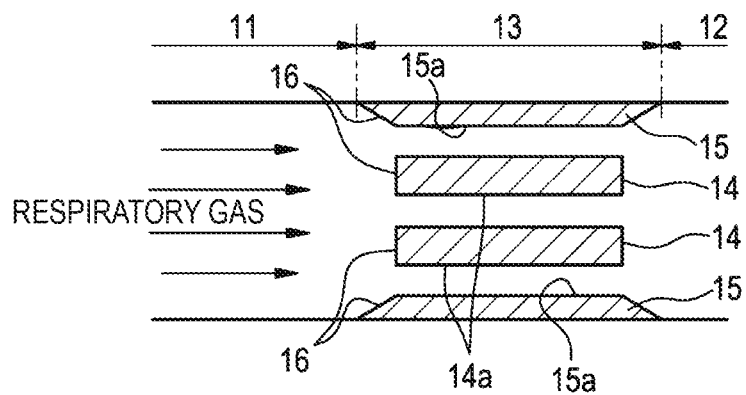
FIGS. 10A and 10B are views illustrating the function of the configuration of the presently disclosed subject matter.
Figure 10B:
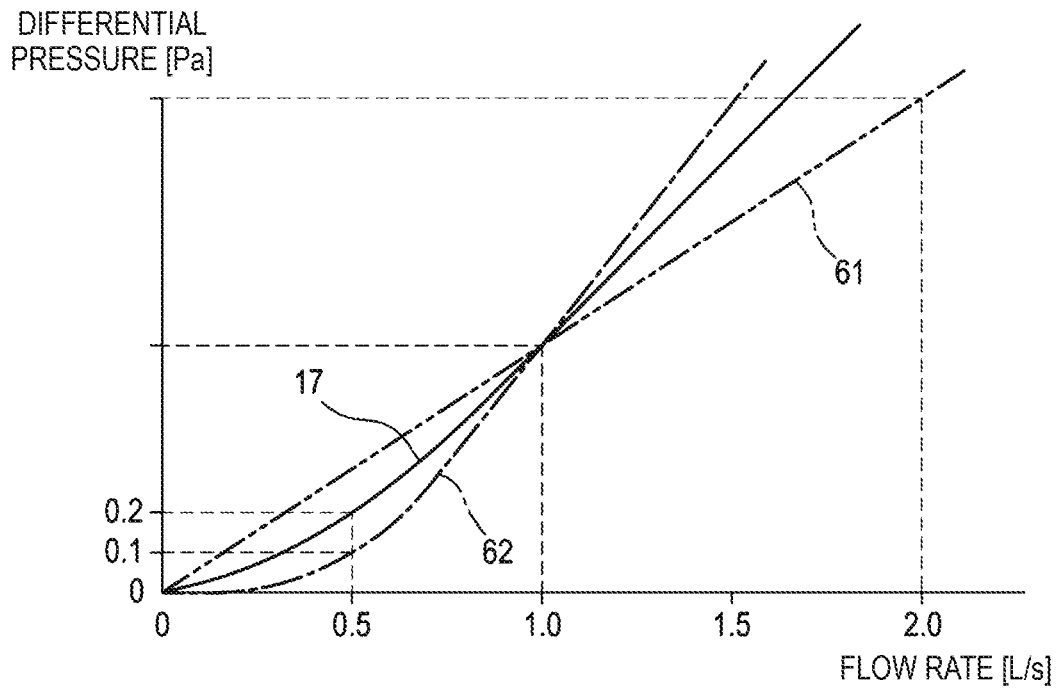

As illustrated in FIG. 10A, therefore, the plate-like members 14 having the side surfaces 14a which extend along the flow direction of the respiratory gas are placed between the projections 15. In the configuration, the end surfaces 16 of the plate-like members 14 and the projections 15, the side surfaces 14a of the plate-like members 14, and the side surfaces 15a of the projections 15 are elements which generate a resistance to the flow of the respiratory gas. As a result of actual measurements, the inventor has found that, when the areas of the end surfaces 16 (the aperture of the attaching-section gas passage 13a) are changed, the resistance to the respiratory gas is largely increased in the same manner as described above, and, when the areas of the side surfaces 14a are changed, by contrast, the relationship (the quadratic function curve) between the differential pressure and the flow rate can be adjusted while preventing the resistance to the respiratory gas from being increased. The inventor has further found that, when the adjustment is performed, while the value of the differential pressure in the range of a flow rate of 1.0 [L/S] or less is made close to the linear function line 61, the value of the differential pressure in the range of a flow rate of 1.0 [L/S] or more can be maintained at a value which is close to the linear function line 61, as indicated by a quadratic function curve 17 in FIG. 10B.

According to the configuration of the presently disclosed subject matter, as the resistance portion, the at least two plate-like members 14 are disposed in the gas passage along the axial direction of the tubular member 10 in the state where the plate-like members are separated from one another by a predetermined distance. In this case, it is considered that, because of not only the resistance due to the end surfaces 16 of the plate-like members 14 and the projections 15 which intersect substantially perpendicularly with the axial direction of the tubular member 10, but also the side surfaces 14a of the plate-like members 14 and side surfaces 15a of the projections 15 which extend along the axial direction, a pressure loss of a given level or higher is generated in the respiratory gas flowing through the attaching-section gas passage 13a. When the surface areas of the side surfaces 14a are increased while maintaining the surface areas of the end surfaces 16 (the size of the attaching-section gas passage 13a in the form of apertures) of the end surfaces 16, therefore, a differential pressure signal which is necessary for measuring a relatively small ventilation volume can be obtained while the resistance in the attaching-section gas passage 13a prevented from being increased. As a result, even when noises are caused in the differential pressure output by external factors or the like, the flow rate which is calculated based on the differential pressure is less varied, and has a relatively stable value.

Since the side surfaces 14a of the plate-like members 14 are disposed parallel to the axial direction of the tubular member 10, moreover, a differential pressure signal which is necessary for measuring a relatively small ventilation volume can be obtained while further preventing the resistance in the attaching-section gas passage 13a from being increased.

Since the plate-like members 14 are disposed parallel to each other, moreover, a necessary differential pressure signal can be obtained while further preventing the resistance from being increased.

Furthermore, the holes 14b which allow the detection light beams that is emitted from the outside of the tubular member 10, to pass through the holes are formed in the plate-like members 14, respectively. When, for example, an optical sensor is attached, therefore, it is possible to measure the concentration of a gas contained in the expiration of the subject, such as carbon dioxide.

Inside the first adaptor connecting portion 11*b* the size of which is set in accordance with the standard, the first adaptor gas passage 11*a* is formed that corresponds in size to the attaching-section gas passage 13*a* in which the plate-like members 14 are disposed. Inside the second adaptor connecting portion 12*b*, similarly, the second adaptor gas passage 12*a* is formed. Therefore, it is possible to form a gas passage having a capacity which is suitable for a subject in whom the ventilation volume in one respiration is small, such as an infant, a baby, or an aged person.

Figure 11:
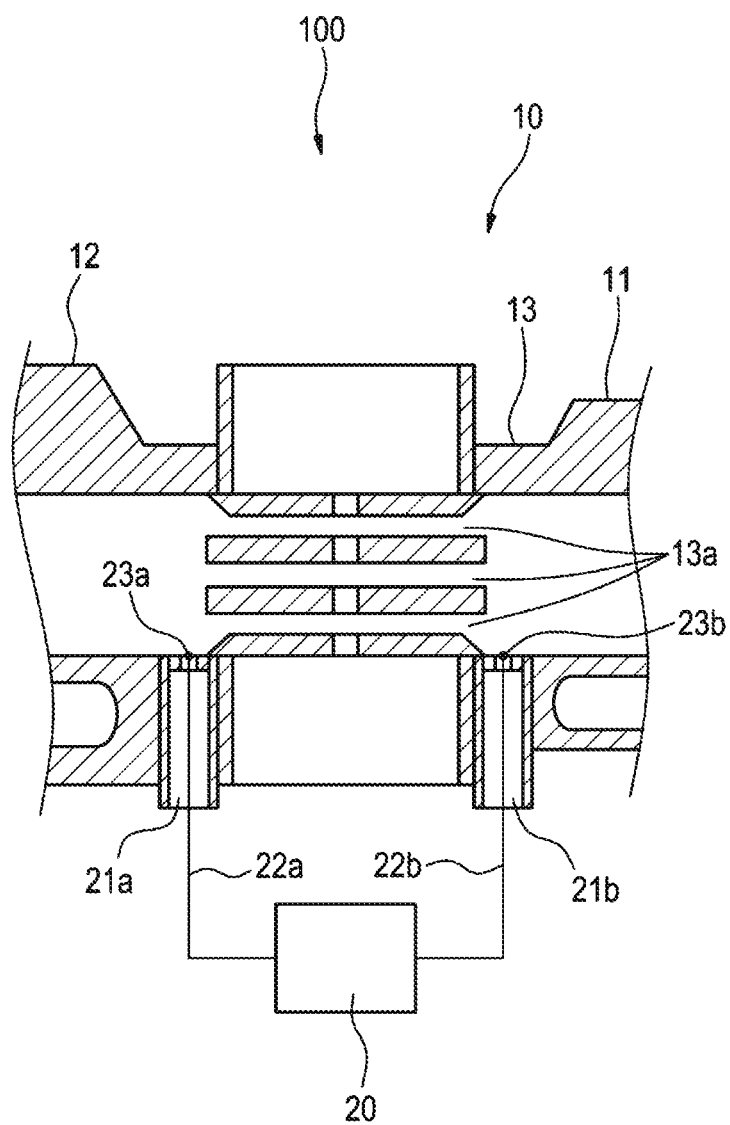
FIG. 11 is a view illustrating an airway adaptor to which a measuring section is attached.

When a measuring section 20 which measures the flow rate of the respiratory gas is attached to the tubular member 10 as illustrated in FIG. 11, the airway adaptor 1 can be configured as a respiratory flow rate sensor 100.

The measuring section 20 is attached to the tubular member through the pressure take-out ports 21*a*, 21*b* of the attaching section 13. One-end sides of pressure ports 22*a*, 22*b* are placed so as to be projected into the attaching-section gas passage 13*a* through respective openings 23*a*, 23*b* (see FIGS. 2 and 7) of the pressure take-out ports 21*a*, 21*b*. The other end sides of the pressure ports 22*a*, 22*b* are connected to the measuring section 20 through the respective pressure take-out ports 21*a*, 21*b*. The pressure across the ends of the plate-like members 14 in the flow direction of the respiratory gas is sensed via the pressure ports 22*a*, 22*b*, the differential pressure is detected by the measuring section 20, and the flow rate of the respiratory gas flowing through the tubular member 10 is calculated.

According to the configuration, when an infant, a baby, or an aged person is ventilated, the medical person can determine whether the ventilation is appropriately performed or not, not by means of a visual check, but based on the output value of the respiratory flow rate sensor.

Figure 12:
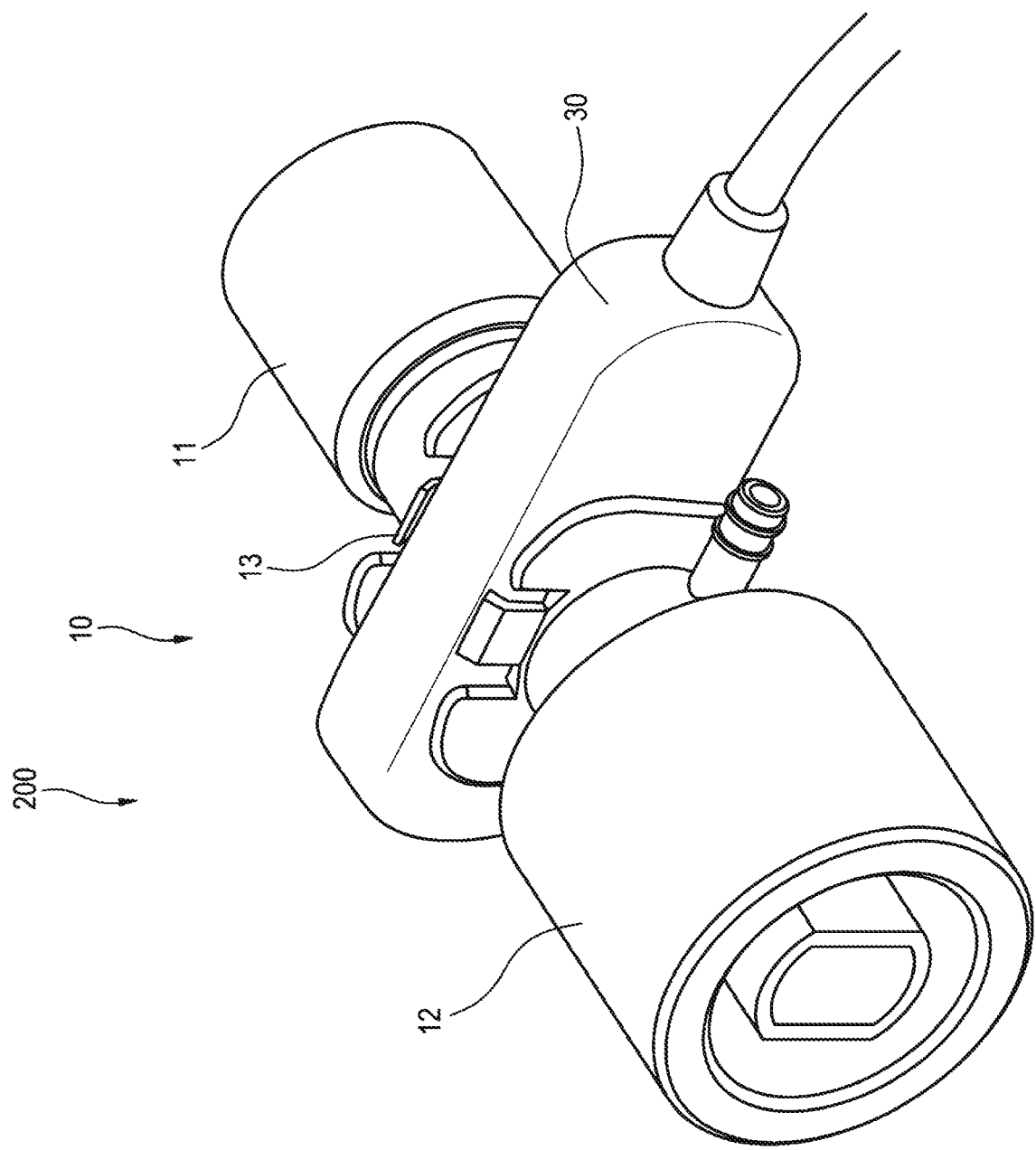
FIG. 12 is a view illustrating an airway adaptor to which a measuring section that is different from that shown in FIG. 11 is attached.

When a measuring section 30 which measures the concentration of a specific component of the respiratory gas is attached to the tubular member 10 as illustrated in FIG. 12, the airway adaptor 1 can be configured as a respiratory gas concentration sensor 200.

A recess (not shown) which opens into, for example, a rectangular shape is formed in the measuring section 30. The measuring section 30 is attached so as to clamp the attaching section 13 in a direction perpendicular to the axial direction of the tubular member 10, through the recess. A light emitter (an LED or the like) and a light receiver are disposed in the recess of the measuring section 30. When the measuring section is attached to the tubular member, the light emitter and the light receiver are placed at positions which are outside the windows 15*b* of the attaching section 13, respectively. An infrared light beam emitted from the light emitter traverses the attaching-section gas passage 13*a* while passing through the windows 15*b* of the attaching section 13 and the holes 14*b* of the plate-like members 14. In accordance with the concentration of a gas (for example, carbon dioxide) contained in the respiratory gas flowing through the attaching-section gas passage 13*a*, the absorption amount of the infrared light beam is changed, and therefore the intensity of the infrared light beam which is received by the light receiver is changed. When an output signal corresponding to the intensity of the received light beam is monitored, a predetermined gas component contained in the respiratory gas is detected.

According to the configuration, it is possible to measure the concentration of a gas such as carbon dioxide contained in the respiratory gas of the subject who is ventilated through the airway adaptor 1.

The foregoing description of the embodiment has been made in order to facilitate understanding of the presently disclosed subject matter, and is not intended to limit the presently disclosed subject matter. It is a matter of course that the presently disclosed subject matter may be changed or improved without departing the spirit thereof, and includes equivalents thereof.

Figure 13A:
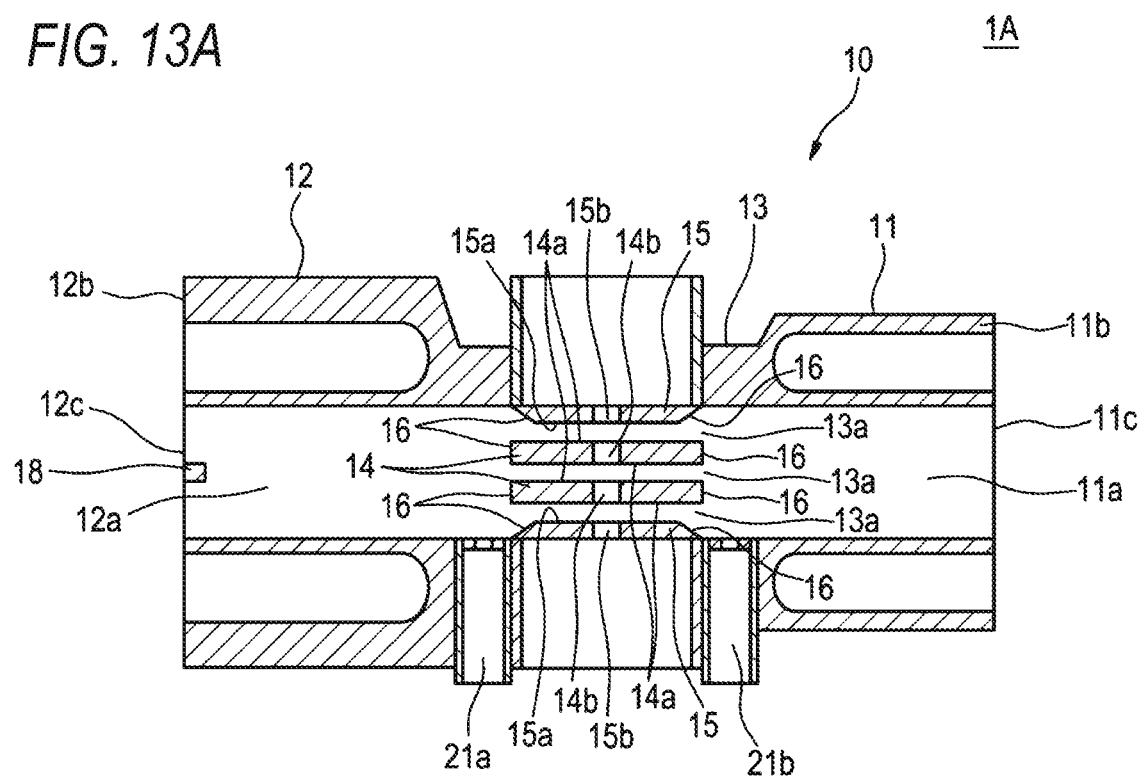
FIG. 13A is a sectional view of a modification of the airway adaptor.
Figure 13B:
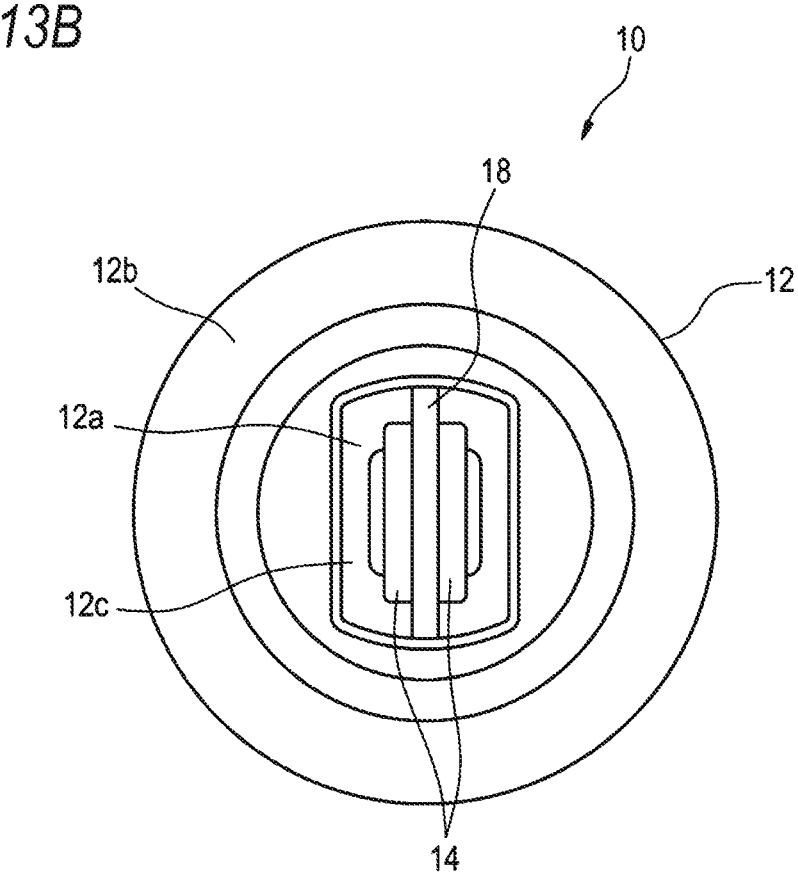
FIG. 13B is a left side view of the modification.

For example, FIGS. 13A and 13B illustrate an airway adaptor 1A of a modification. In the airway adaptor 1A, a diffusing portion 18 is disposed inside the opening 12*c* of the second adaptor gas passage 12*a*. The airway adaptor 1A is configured in the same manner as the above-described airway adaptor 1 except the disposition of the diffusing portion 18. The diffusing portion 18 in the modification is a rod-like member, and formed integrally with the second adaptor gas passage 12*a* to partition the opening 12*c* into two areas. The diffusing portion 18 has a function of preventing a jet stream from being generated in the second adaptor gas passage 12*a*. The shape and placement of the diffusing portion 18 may be adequately changed as far as they enable the diffusing portion to prevent a jet stream from being generated.

Figure 14:
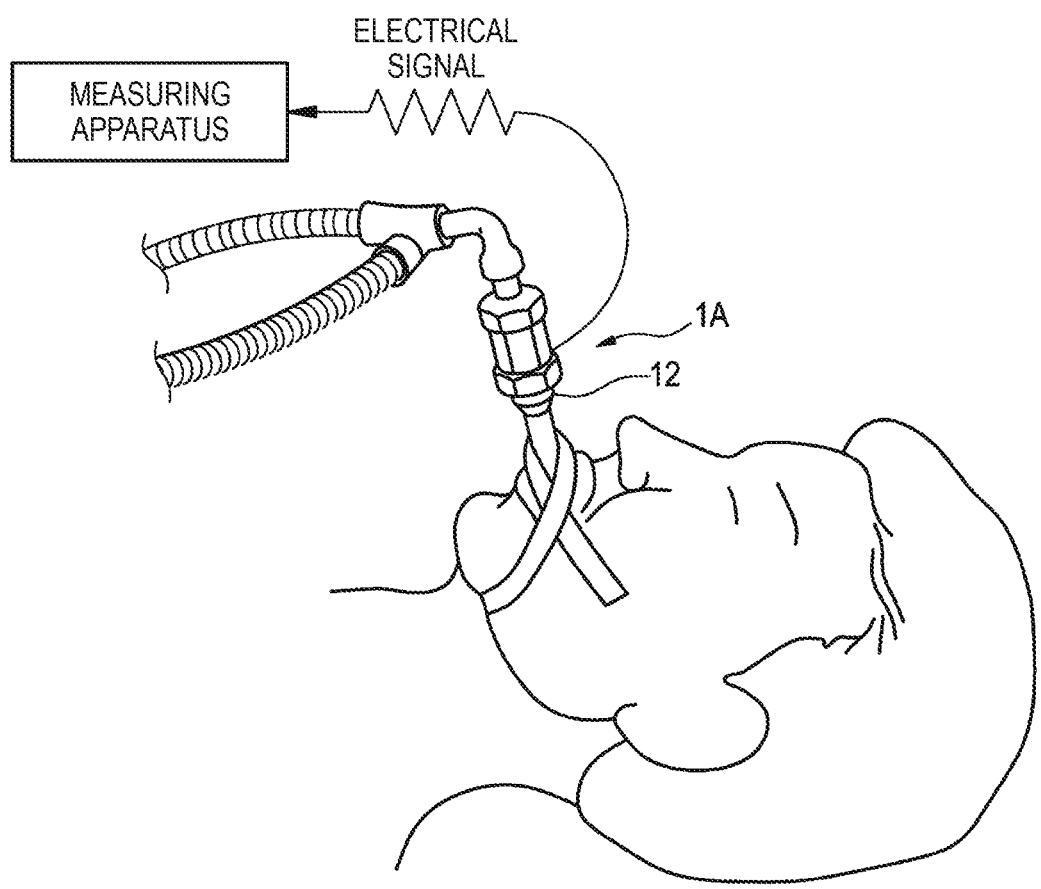
FIG. 14 is a view illustrating a use example of the airway adaptor of the modification.

The airway adaptor 1A exemplified in FIGS. 13A and 13B is suitably used in an intubation tube. FIG. 14 illustrates a use example of the airway adaptor 1A. In the case where an intubation tube having a relatively small inner diameter is used, usually, there is a fear that a jet stream is generated in an airway adaptor, and the accuracy of measurement of the ventilation volume is lowered by the influence of the jet stream. In the airway adaptor 1A exemplified in FIGS. 13A and 13B, however, the diffusing portion 18 prevents a jet stream from being generated in the second adaptor gas passage 12*a*, and therefore the accuracy of measurement of the ventilation volume is hardly lowered.

In a related-art differential pressure flowmeter, when the sensitivity or accuracy of the flow rate measurement is to be adjusted, the adjustment is performed by adjusting the size of the opening of the orifice plate. In this method, in accordance with the adjustment of the size of the opening, the resistance to the fluid is easily changed.

According to an aspect of the presently disclosed subject matter, as the resistance portion, the at least two partition members are disposed in the gas passage along the axial direction of the tubular member in a state where the partition members are separated from one another by a predetermined distance. In this case, because of not only the resistance due to end surfaces of the partition members which intersect substantially perpendicularly with the axial direction of the tubular member, but also the side surfaces of the partition members which extend along the axial direction, the partition members generate a pressure loss of a given level or higher in the fluid (the expiration or the inspiration) flowing through the gas passage. In a state where the amount of the fluid flowing through the gas passage is small, when a pressure loss of a given level or higher is to be generated in the gas passage, for example, it is contemplated that the degree of a change in the resistance which is caused when the pressure loss is generated by increasing the areas of the side surfaces is smaller than that of a change in the resistance which is caused when the pressure loss is generated by increasing the areas of the end surfaces. When the partition members are disposed and placed along the axial direction of the tubular member, therefore, it is possible to obtain a differential pressure signal which is necessary for measuring a relatively small ventilation volume, while preventing the resistance of the gas passage from being increased.

What is claimed is:

1. An airway adaptor to which a measuring section configured to measure a flow rate of a respiratory gas of a subject is to be attached, the airway adaptor comprising:
   a tubular member having a gas passage through which the respiratory gas passes, the tubular member comprising first and second opposing portions and a middle portion disposed between and connecting the first and second opposing portions in a longitudinal axial direction of the tubular member; and
   a resistance portion disposed within the gas passage and positioned at the middle portion of the tubular member without extending into the first and second opposing portions of the tubular member, the resistance portion configured to generate a differential pressure in the respiratory gas passing through the gas passage, wherein:
   the resistance portion includes at least two partition members which are disposed in the gas passage, the at least two partition members which extend along the longitudinal axial direction of the tubular member and the at least two partition members which are separated from an inner wall surface of the gas passage in a direction that is transverse to the longitudinal axial direction of the tubular member, the at least two partition members which are separated from one another and which are disposed parallel to each other so that an interior of the tubular member is partitioned into a plurality of gas passages which are juxtaposed to one another so as to extend along the longitudinal axial direction of the tubular member,
   the gas passage includes a main gas passage, a first adaptor gas passage, and a second adaptor gas passage, the main gas passage including the at least two partition members therein, the main gas passage positioned between the first adaptor gas passage and the second adaptor gas passage in the longitudinal axial direction of the tubular member, the main gas passage formed with pressure take-out ports which are disposed in both end sides of the main gas passage in the longitudinal axial direction of the tubular member, the measuring section to be attached to the airway adaptor through the pressure take-out ports,
   the at least two partition members are disposed inside of a range between the pressure take-out ports in the longitudinal axial direction of the tubular member without extending into the first and second adaptor gas passages,
   each of the at least two partition members has a first maximum length in the longitudinal axial direction and a second maximum length in the direction that is transverse to the longitudinal axial direction, wherein the first maximum length is greater than the second maximum length.

2. The airway adaptor according to claim 1, wherein side surfaces of the at least two partition members are separated from the inner wall surface of the gas passage and are parallel to the longitudinal axial direction of the tubular member.

3. The airway adaptor according to claim 1, wherein a hole allowing a detection light beam which is to be emitted from an outside of the tubular member, to pass through the hole is formed in each of the at least two partition members.

4. The airway adaptor according to claim 1, wherein
   the tubular member includes: a first adaptor section disposed in one end side of the tubular member and including the first adaptor gas passage, and a second adaptor section disposed in the other end side of the tubular member and including the second adaptor gas passage,
   the first adaptor section is provided for connecting to an inspiration supplying section for supplying the respiratory gas to the subject, and
   the second adaptor section is provided for connecting to an expiration outputting section for outputting the respiratory gas from the subject.

5. A respiratory flow rate sensor comprising:
   the airway adaptor according to claim 1; and
   the measuring section.

6. The airway adaptor according to claim 1, wherein
   the tubular member includes: a first adaptor section disposed in one end side of the tubular member and including the first adaptor gas passage, and a second adaptor section disposed in the other end side of the tubular member and including the second adaptor gas passage,
   the first adaptor section includes a first adaptor connecting portion which is formed to cover an outside of the first adaptor gas passage, and
   the second adaptor section includes a second adaptor connecting portion which is formed to cover an outside of the second adaptor gas passage.

7. The airway adaptor according to claim 1, the at least two partition members being separated from one another in the direction that is transverse to the longitudinal axial direction of the tubular member.

8. The airway adaptor according to claim 1, the at least two partition members being positioned adjacent one another in the direction that is transverse to the longitudinal axial direction of the tubular member.

9. The airway adaptor according to claim 1, wherein the gas passage at a middle portion of the resistance portion is narrower than the gas passage at an end portion of the resistance portion in the longitudinal axial direction of the tubular member.

10. The airway adaptor according to claim 1, wherein the second adaptor gas passage includes a diffusing portion therein, the diffusing portion configured to diffuse air passing through the second adaptor gas passage, and wherein the diffuser portion is configured to prevent a jet stream from being generated in the second adaptor gas passage.

* * * * *

UNITED STATES PATENT AND TRADEMARK OFFICE
CERTIFICATE OF CORRECTION

| | |
|---|---|
| PATENT NO. | : 11,850,036 B2 |
| APPLICATION NO. | : 15/266463 |
| DATED | : December 26, 2023 |
| INVENTOR(S) | : Fumihiko Takatori |

It is certified that error appears in the above-identified patent and that said Letters Patent is hereby corrected as shown below:

In the Specification

Column 4, Line 9, "axis. measuring section" should read -- axis. A measuring section --

Column 5, Line 34, "FIB. 98 Ina range" should read -- FIG. 9B. In a range --

Column 5, Line 63, "length to in addition to" should read -- length Lo in addition to --

Column 6, Line 45, "13a prevented from being" should read -- 13a is prevented from being --

Signed and Sealed this
Twelfth Day of November, 2024

Katherine Kelly Vidal
*Director of the United States Patent and Trademark Office*